(12) United States Patent
Srinivasa et al.

(10) Patent No.: US 6,657,082 B2
(45) Date of Patent: *Dec. 2, 2003

(54) PROCESS FOR THE PREPARATION OF THIOUREA

(75) Inventors: Balakrishnan Srinivasa, Pune (IN); Mahajan Shankar Shivram, Pune (IN); Chaphekar Gopal Moreshwar, Pune (IN); Gupte Milind Yeshwant, Pune (IN); Kulkarni Mohan Parshuram, Pune (IN); Bandarupalli Radha Krishna Murthy, Pune (IN)

(73) Assignee: Council of Scientific and Industrial Research, New Delhi (IN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 172 days.

(21) Appl. No.: 09/046,740

(22) Filed: Mar. 24, 1998

(65) Prior Publication Data

US 2003/0060662 A1 Mar. 27, 2003

(51) Int. Cl.⁷ ............................................. C07C 335/02
(52) U.S. Cl. ........................................... 564/25; 564/17
(58) Field of Search ..................................... 564/25, 17

(56) References Cited

U.S. PATENT DOCUMENTS 1,977,210 A * 10/1934 Schulenberg ................ 564/25
2,337,882 A * 12/1943 Gajewski .................... 564/25
2,353,997 A * 7/1944 Cooper ....................... 564/25
3,501,524 A * 3/1970 Krulik et al .................. 564/25

* cited by examiner

Primary Examiner—Shailendra Kumar
(74) Attorney, Agent, or Firm—Caesar, Rivise, Bernstein, Cohen & Pokotilow, Ltd.

(57) ABSTRACT

The present invention relates to an improved process for the preparation of thiourea. The object of the present invention is to provide an improved process for the preparation of Thiourea using Calcium Cyanamide, carbon dioxide and hydrogen sulphide. The process of the present invention comprises passing a mixture of Carbon dioxide and hydrogen sulphide into a slurry formed by addition of major part of calcium cyanamide charge into water using constant stirring, maintaining alkaline pH at a temperature ranging between ambient to 80° C., stopping the addition of hydrogen sulphide, continuing the slow passing of carbon dioxide and addition of remaining part of calcium cyanamide charge and retaining the reaction mass to complete the secondary reactions to form the product for a period ranging from 2–5 hours and continuing passing of carbon dioxide at an increased rate for effecting decomposition of $Ca(SH)_2$ for a period of 1.6 to 6 hours, stopping the addition of carbon dioxide separating thiourea solution, treating the separated solution with activated carbon, removing the carbon by conventional methods, separating the product formed by conventional methods and drying the product at a temperature between 50–70° C. to obtain the product.

9 Claims, No Drawings

PROCESS FOR THE PREPARATION OF THIOUREA

FIELD OF THE INVENTOIN

This invention relates to an improved process for the preparation of thiourea.

BACKGROUND OF THE INVENTION

Thiourea finds application in manufacture of amino resins, herbicides, fungicides, insecticides, plant growth regulators, photographic paper. It finds use in electrochemical processes, pharmaceutical industries, textile processing, hydrometallurgy, rubber industry and petroleum industry.

In the prior art thiourea is presently produced essentially by the following methods.

(a) from ammonium sulphocyanide by isomerisation in molten condition:
(b) from Calcium Cyanamide and ammonium sulphide:
(c) from Calcium Cyanamide and calcium hydrosulphide:
(d) from Calcium Cyanamide and hydrogen sulphide and subsequent conversion by method (c).

The above mentioned processes are briefly described herein-below.

(a) The isomerisation of ammonium sulphocyanide involves melting the ammonium thiocyanate and keeping upto temperature level of 140–170° and dissolving the thiocarbamide from the cooled ground melt.

$$NH_4SCN \rightarrow CS(NH_2)_2$$

(b) The preparation by the reaction between calcium cyanamide and ammonium sulphide involves addition of the solution of the latter at 25–80° C. and blowing off ammonia, or in the presence of an ammonium salt such as carbonate, sulphate or oxalate.

(c) The calcium hydrosulphide method involves addition of cyanamide to a solution of calcium hydrosulphide such that the temperature is controlled around 70–80° C. The reaction is:

$$2CaCN_2 + Ca(SH)_2 + 6H_2O \rightarrow 3Ca(OH)_2 + 2CS(NH_2)_2$$

The product is isolated from the reaction mass by filtration, concentration at temperatures below 98°, filtration to remove calcium salts and crystallisation.

(d) The method using reaction between calcium cyanamide and hydrogen sulphide consists of passing a current of hydrogen sulphide in a suspension of calcium cyanamide with good agitation and avoiding undue rise in temperature.

The reaction is:

$$CaCN_2 + 3H_2S \rightarrow Ca(SH)_2 + CS(NH_2)_2$$

The $Ca(SH)_2$ is converted into thiourea by further addition of calcium cyanamide according to the following reaction.

$$2CaCN_2 + Ca(SH)_2 + 6H_2O \rightarrow 2CS(NH_2)_2 + 3Ca(OH)_2$$

Besides the above the other methods include the following.

(a) Treatment of $CaCN_2$ with $H_2S$ in the presence of small amount of water, methanol, ethylacetate, aniline or esters, hydrocarbons like benzene or their halogen derivatives.
(b) Reacting together $CaCN_2$ and alkaline earth sulphide in presence of water and carbon dioxide in a ball mill.
(c) Reacting alkaline earth cyanamide such as $CaCN_2$ with $SO_2$ or $CO_2$ till calcium is removed and making alkaline with ammonia and further reaction with $H_2S$ and completion of the reaction by heating.
(d) Converting $CaCN_2$ by hydrolysis to $Ca(HCN_2)_2$ and passing $H_2S$ and subsequent treatment to remove calcium by $CO_2$ containing gases.
(e) Treating $CaCN_2$ in water with sulphuric acid at low temperatures, making ammoniacal and treatment with $H_2S$ at low temperature and acidifying and cooling.
(f) By reaction between cyanamide and $Na_2S$ in aqueous phosphate or borate buffers at pH 6–10 at 25° C.
(g) By simultaneous action of $CO_2$ and $H_2S$ in high $H_2S$ ratios on aqueous suspension of calcium cyanamide.
(h) Reaction of $As_2S_3$ ore in presence of sulphur with $CaCN_2$ such that the ratio of Nitrogen and S are in the ratio 1:1.

The above methods suffer from the following draw-backs:

1. The isomerisation methods given conversions only upto a maximum of 25% at the most and isolation involves tedious methods.
2. Ammonium sulphide is not commercially available and the method involving its use produces ammonia. Impurities like sulphate are also present.
3. The method using calcium hydrosulphide or hydrogen sulphide produces lime and its removal completely is not possible. Impurities like calcium trithiocarbonate and calcium sulphocyanide are formed. This requires discarding of mother liquors where thiourea is lost. Formation of calcium hydroxide is detrimental to the product.
4. The reaction between calcium cyanamide and hydrogen sulphide suffers from the following counts:
   a) The consumption of hydrogen sulphide is high and produces equimolar quantity of calcium hydrosulphide.
   b) The calcium hydrosulphide on reaction with calcium cyanamide produces calcium hydroxide which is difficult to remove as stated in (3) above.
5. The process which use simultaneous use of $CO_2$ and $H_2S$ consume a large amount of expensive and toxic $H_2S$ and no recovery of the unused $H_2S$ is indicated. The auto-genous temperature rise may give rise to sulphur components other than thiocarbamide.
6. Methods involving use of $As_2S_3$ and $Na_2S$ are of limited use and applications due to very stringent reaction conditions.

SUMMARY OF THE INVENTION

The object of the present invention is to provide an improved process for the preparation of Thiourea using Calcium Cyanamide, carbon dioxide and hydrogen sulphide.

Accordingly the present invention provides an improved process for the preparation of thiourea which comprises passing a mixture of carbon dioxide and hydrogen sulphide into a slurry formed by addition of major part of calcium cyanamide charge into water under constant stirring, maintaining alkaline pH at a temperature ranging between ambient to 80° C., stopping the addition of hydrogen sulphide, continuing the slow passing of carbon dioxide and addition of remaining part of calcium cyanamide charge and retaining the reaction mass to complete the secondary reactions to form the product for a period ranging from 2 to 5 hours and continuing passing of carbon dioxide at an increased rate for effecting decomposition of $Ca(SH)_2$ for a period of 1.6 to 6 hours, stopping the addition of carbon dioxide, separating thiourea solution by conventional methods, treating the separated solution with activated carbon, removing the carbon by conventional methods, separating the product formed by conventional methods and drying the product at a temperature between 50 to 70° C. to obtain the product.

DETAILED DESCRIPTION OF PREFERED EMBODUIMENTS

In an embodiment of the present invention the pH of the reaction mixture maintained may be at a value 8.0 to 11.0.

In another embodiment of the present invention the rate of addition of carbon dioxide may range between 2.0 to 3.33 gm moles per hour per kg charge of calcium cyanamide during the simultaneous passage of hydrogen sulphide.

In another embodiment of the present invention the rate of addition of hydrogen sulphide may range between 2.6 to 3.4 gm moles per hour per kg. charge of calcium cyanamide.

In another embodiment of the present invention, the time of addition of 85–90% of total charge of calcium cyanamide may range between 1.8 to 2.2 hour.

In another embodiment of the present invention the time of addition of 10–15% of total charge of calcium cyanamide may range btween ½ to 1 hour.

In another embodiment of the present invention the reaction mixture after the addition of 15% of total charge may be kept under a small feed of carbon dioxide ranging from 0.32 to 1.0 gm mole per hour per kg charge of calcium cyanamide.

In another embodiment of the present invention the reaction mass may be retained for a period ranging from 2 to 5 hours after the addition of calcium cyanamide is complete.

In yet another embodiment of the present invention, the rate of addition of carbon dioxide for decomposition of $Ca(SH)_2$ may range from 0.8 to 2.5 gm moles per hour per kg charge of calcium cyanamide.

In a feature of the present invention the calcium carbonate is removed by conventional methods like filtration and the product is recovered by treating the filtrate with activated carbon at 60 to 80° C., and subsequent evaporation under reduced pressure and crystallisation at 10–15° C. The pressure employed may range from 55 to 65 mm Hg at a temperature of 50 to 70° C.

The crystals are filtered and washed with water at 0 to 5° C. and dried at 50–80° C. The washings of crystals can be recycled to evaporator.

The conversion of thiourea based on calcium cyanamide is 85–92.5% and the yields of the product range from 65–75% with purities ranging 95–98% based on a single crop. Selectivity based on hydrogen sulphide fed is 72–72.5% and 100% on hydrogen sulphide consumed in all cases.

In another feature of the present invention the process can be used even with mother liquors containing thiourea obtained after crystallising it. The quality of the product is comparable with that obtained from the customary process once through.

The invention is illustrated by the following examples, which may not be construed to limit the scope of this invention in any manner whatsoever.

EXAMPLE 1

In a five necked cylindrical glass reactor of 3 liter capacity, 2.4 liter of water was filled and was kept agitated vigorously. It was kept in water bath. Hydrogen sulphide and carbon dioxide were fed at a regulated rate and 600 gm of calcium cyanamide ($CaCN_2$ 42.0% CaO 34.06%) was added slowly. Hydrogen sulphide was passed at a rate of about 57.5 gm per hour and carbon dioxide was passed at a rate of 50.0 gm per hour and were measured by suitable flow meters. About 85% of total calcium cyanamide was added during 130 minutes and total hydrogen sulphide passed was 126.4 gm (18% excess over theory). Carbon dioxide passed during this period was 133.8 gm. During the above reaction the pH varied from 8.6–9.7 and the temperature varied from 29–56° C. The hydrogen sulphide was stopped but carbon dioxide was passed at a rate of 21.5 gm per hour and the balance calcium cyanamide was added. The total duration was 170 minutes. During passing the carbon dioxide gas the pH ranged from 8.6–9.1 and the temperature ranged between 32–35° C.

The reaction mass was then treated with 98 gms of carbon dioxide for 100 minutes till sulphide was absent by usual tests.

The temperature was kept between 40–65° C. during this operation.

The final mass on filtration under suction and washing with 1.25 liter hot water yielded 3.73 liter of filtrate. On analysis of the filtrate and the solids the conversion to thiourea was found to be 85.0 on $CaCN_2$ content of charge.

The filtrate on concentration in vacua to 400 ml volume on cooling to 10° C. yielded 145.5 gm (yield 69.05%) crystals which assayed to 98.0% thiourea. The mother liquor was discarded. The selectivity based on hydrogen sulphide fed was 72.0%.

EXAMPLE 2

Six hundred grams of calcium cyanamide ($CaCN_2$ 42.0% CaO 34.06% was charged into 2.4 liter water and treated with 129.0 gm of hydrogen sulphide (20.6% excess over theory) and also 150 gm of carbon dioxide for 2.25 hours followed by 15 gm of carbon dioxide for 2 hours and finally by 104.5 gm carbon dioxide for 2.25 hours till sulphide was absent:

Further processing such as filtration under suction and washing with 1.15 liter of hot water yielded a filtrate of 3.61 liter. On analysis the conversion was found to be 90.76% on $CaCN_2$ content.

The temperature ranged from 21°–60° and pH 8.8–9.6.

The filtrate on treatment with 55 gm of decolorising charcoal at 60°–80° C. for 30 minutes, filtration, concentration in vacua to 450 ml and cooling to 15° C. yielded 158 gm of thiourea (66.0% yield) and of purity 98.4% on assaying selectivity based on hydrogen sulphide fed was 75.4%.

EXAMPLE 3

Six hundred gms of calcium cyanamide ($CaCN_2$ 42.0%, CaO 34.06%) was charged into a mixture of 280 ml of mother liquor containing 31.28 gms of thiourea and 18.95 gms of the solids from a previous batch and 2.120 ml water on treatment with 132.8 gm of hydrogen sulphide (excess 24.1%) and 167 gm of carbon dioxide for 155 minutes, followed by 8.1 gm carbon dioxide for 55 minutes and 129.5 gm of carbon dioxide for 160 minutes till sulphide was absent yielded a filtrate of 3.25 liter on processing as usual. The conversion to thiourea on $CaCN_2$ was found to be 90.47% as analysis of filtrate and filter cake.

The pH varied from 8.8–9.7 and the temperature ranged from 28–65° C. The filtrate on concentration under vacua to 375 ml and cooling to 10° C. yielded crystals of 175.0 gm of thiourea (yield 73.1%) assaying 95.6%. The selectivity based on hydrogen sulphide fed was 73.0%.

EXAMPLE 4

In metallic reactor of 250 liter capacity with jacket, stirrer, gas spargers, solid feeding arrangement, continuous pH measuring and temperature measuring devices, 160 liter of water was kept circulated by a powerful pump. Forty Kg of calcium cyanamide ($CaCN_2$ 46.3%, CaO 35.88%) was added slowly with 8.0 kg of hydrogen sulphide (9.89% excess) and 10.6 kg carbon dioxide for 120 minutes. About 85% of total calcium cyanamide was added during the above period.

The feed of hydrogen sulphide was stopped, balance of 15% of calcium cyanamide was added over a period of 40 minutes and 2.3 kg of carbon dioxide was passed for 240 minutes.

Then 8.5 kg of carbon dioxide was passed for 6 hours for sulphide removal. Cooling water was kept running in the jacket. The pH ranged from 8.5–9.3 and temperatures 31–42° C.

Filtration and washing with 90 liter water in a vacuum rotary drum yielded 245 liter of filtrate. The conversion to thiourea was 92.5% including the thiourea in filter cake (61 kg wet).

This filtrate along with 10 liter of crystal wash from previous batch containing 600 gm thiourea on evaporation under vacuum to 36 liter and crystallising at 12° C. and washing with ice-cold water at 0–5° C. yielded 12.2 kg of thiourea (69.3% yield). Purity on assaying was found to be 97.6%.

Selectivity based on hydrogen sulphide feed was 91.0%.

EXAMPLE 5

A 40 kg quantity of calcium cyanamide assaying 37.6% $CaCN_2$ with 160 liter water, 7.4 kg (110 minutes) and total 17.1 kg carbon dioxide was passed at 8.5 kg for 135 minutes, 1.8 kg in 270 minutes and 6.0 kg in 360 minutes for reaction, retention and sulphide removal respectively, in the apparatus previously described, indicated a conversion of 88.2% to thiourea on $CaCN_2$, a yield of 68%, purity of 97.8% and a selectivity on hydrogen sulfide of 86.4%.

The main advantages of the present invention are:

1) Very good yield in the range of 65–75% of Thiourea.
2) Isolation of the thiourea formed by conventional methods.
3) Elimination of chemicals like $(NH_4)_2S$ which are not commercially available.
4) Selectivity based on the hydrogen sulphide fed in the range of 72–91% and 100% on the basis of hydrogen sulphide consumed.
5) Product obtained by the improved process is of very high purity in the range of 95.6–98%.
6) Conversion based on calcium cyanamide in the range of 85–92.5% of thiourea.
7) Calcium cyanamide of low assay could also be used to produce thiourea of good quality.
8) The reaction is carried out with very low excess of hydrogen sulphide which prevents the formation of other sulphurcompounds.
9) The excess of hydrogen sulphide used is between 10–25% over theory as against 50–100 which is common practice.
10) The addition of calcium cyanamide being slow and controlled does not allow the formation of by-products like dicyanamide.
11) The conditions of the reaction are more conducive to formation of $SH^-$ ions which are essential for the formation of thiourea.
12) The reaction schemes involved using calcium cyanamide, carbon dioxide and hydrogen sulphide are simple and yet novel.

We claim:

1. An improved process for preparing thiourea, said process comprising:
    (a) providing a reaction vessel containing a slurry comprising water and a major part of a calcium cyanamide charge;
    (b) sparging carbon dioxide and hydrogen sulphide into said slurry;
    (c) maintaining a pH of said slurry alkaline;
    (d) providing said slurry at an initial temperature of at least about room temperature and permitting said slurry to achieve a process temperature of at least 56° C. and not more than 80° C;
    (e) stopping said hydrogen sulphide sparging while maintaining said carbon dioxide sparging;
    (f) adding a remaining part of said calcium cyanamide charge to said slurry to form a reaction mass in said reaction vessel;
    (g) retaining said reaction mass in said reaction vessel for 2 to 5 hours to complete secondary reactions to form thiourea;
    (h) increasing a carbon dioxide sparging rate for a period of 1.6 to 6 hours to effect decomposition of $Ca(SH)_2$;
    (i) terminating said carbon dioxide sparging;
    (j) separating thiourea solution from said slurry; and
    (k) isolating said thiourea from said thiourea solution, wherein calcium cyanamide, carbon dioxide and hydrogen sulphide are the only reagents employed in said process.

2. An improved process as claimed in claim 1 wherein the pH of the slurry is maintained from 8.0 to 11.0.

3. An improved process as claimed in claim 1 or 2 wherein a rate of said carbon dioxide sparging ranges from 2.0 to 3.33 gm. moles per hour per kg. of said calcium cyanamide charge.

4. An improved process as claimed in claim 1 or 2 wherein a rate of said hydrogen sulphide sparging ranges from 2.6 to 3.4 gm. moles per hour per kg. of said calcium cyanamide charge.

5. An improved process as claimed in claim 1 or 2 wherein a rate of said carbon dioxide sparging during said retaining ranges from 0.32 to 1.0 gm mole per hour per kg of the calcium cyanamide charge.

6. An improved process as claimed in claim 1 or 2 wherein a rate of said carbon dioxide sparging for decomposition of $Ca(SH)_2$ ranges from 0.8 to 2.5 gm moles per hour per kg of the calcium cyanamide charge.

7. An improved process for preparing thiourea, said process consisting essentially of:
    (a) providing a reaction vessel containing a slurry comprising water and a major part of a calcium cyanamide charge;
    (b) sparging carbon dioxide and hydrogen sulphide into said slurry;
    (c) maintaining a pH of said slurry alkaline;

(d) providing said slurry at an initial temperature of at least about room temperature and permitting said slurry to achieve a process temperature of at least 56° C. and not more than 80° C.;

(e) stopping said hydrogen sulphide sparging while maintaining said carbon dioxide sparging;

(f) adding a remaining part of said calcium cyanamide charge to said slurry to form a reaction mass in said reaction vessel;

(g) retaining said reaction mass in said reaction vessel for 2 to 5 hours to complete secondary reactions to form thiourea;

(h) increasing a carbon dioxide sparging rate for a period of 1.6 to 6 hours to effect decomposition of $Ca(SH)_2$;

(i) terminating said carbon dioxide sparging;

(j) separating thiourea solution from said slurry; and (k) isolating said thiourea from said thiourea solution.

8. An improved process as claimed in claim 1 wherein a molar ratio of hydrogen sulphide to said calcium cyanamide charge is from 1.1:1 to 1.25:1.

9. An improved process as claimed in claim 8 wherein thiourea is a sole product containing sulphur.

* * * * *